US005451202A

United States Patent [19]

Miller et al.

[11] Patent Number: 5,451,202

[45] Date of Patent: Sep. 19, 1995

[54] CERVICAL TRACTION DEVICE

[75] Inventors: Forrest A. Miller; Robert T. Cardozo, both of Seattle, Wash.

[73] Assignee: Pacific Research Laboratories, Inc., Vashon, Wash.

[21] Appl. No.: 125,471

[22] Filed: Sep. 22, 1993

[51] Int. Cl.$^6$ .................................................. A61F 5/00

[52] U.S. Cl. ......................................... 602/36; 602/35; 606/241

[58] Field of Search ........................ 602/18, 32, 33, 35, 602/36; 601/39; 606/241

[56] References Cited

U.S. PATENT DOCUMENTS

| | | | |
|---|---|---|---|
| 2,633,125 | 3/1953 | Yellin . | |
| 2,658,506 | 11/1953 | Haskell . | |
| 2,940,441 | 6/1960 | Demarest et al. | 602/32 |
| 2,954,026 | 9/1960 | Spinks | 602/32 |
| 3,063,445 | 11/1962 | Ries | 602/32 |
| 3,298,364 | 1/1967 | Radford . | |
| 3,359,976 | 12/1967 | Laval, Jr. | 602/36 |
| 3,662,750 | 5/1972 | Jorgensen | 602/35 |
| 3,856,003 | 12/1974 | Pfluger | 602/33 |
| 4,257,410 | 3/1981 | Flewelling . | |
| 4,282,868 | 8/1981 | Riggs . | |
| 4,356,816 | 11/1982 | Granberg . | |
| 4,407,274 | 10/1983 | Goodley . | |
| 4,466,427 | 8/1984 | Granberg . | |
| 4,531,514 | 7/1985 | McDonald et al. . | |
| 4,534,341 | 8/1985 | Bart et al. . | |
| 4,538,598 | 9/1985 | Gill et al. . | |
| 4,602,619 | 7/1986 | Wolf et al. . | |
| 4,603,689 | 8/1986 | Horner . | |
| 4,608,969 | 9/1986 | Hamlin . | |
| 4,627,423 | 12/1986 | Kampner . | |
| 4,664,101 | 5/1987 | Granberg . | |
| 4,674,485 | 6/1987 | Swanson . | |
| 4,936,399 | 6/1990 | Christman et al. . | |
| 4,971,043 | 11/1990 | Jones | 602/36 |
| 4,987,886 | 1/1991 | McDonald et al. . | |
| 5,024,214 | 6/1991 | Hayes . | |
| 5,052,378 | 10/1991 | Chitwood . | |

FOREIGN PATENT DOCUMENTS

| | | | |
|---|---|---|---|
| 2640500 | 6/1990 | France | 602/36 |
| 2004219 | 12/1993 | Russian Federation | 602/36 |

OTHER PUBLICATIONS

"Braces Today", a Newsletter of the Pope Foundation, Inc., Feb. 1958.

(List continued on next page.)

*Primary Examiner*—Richard J. Apley
*Assistant Examiner*—Jeanne M. Clark
*Attorney, Agent, or Firm*—Christensen, O'Connor, Johnson & Kindness

[57] ABSTRACT

An apparatus for applying cervical traction to a user (22) with a head halter (24) is disclosed. The apparatus includes a frame (24), a tensioner assembly (34), a cord (42), and a pulley (44). The frame has a generally straight section (28), a curved section (32), and a shoulder brace (30). The straight section has a head portion (68) extending behind the head of the user and a tail portion (70) extending behind at least a portion of the back of the user. The shoulder brace is coupled to the straight section at the end of the head portion opposite the connection to the curved section and is oriented generally transverse to the longitudinal axis of the straight section. The curved section generally forms a C-shape. The C-shape of the curved section opens toward the head of the user. The tensioner assembly is coupled to the end of the curved section opposite the attachment to the straight section. The tensioner assembly is also coupled to the halter through the cord. The tensioner assembly includes a rotatable axle (38), a handle (36) attached to the axle, and a ratchet mechanism (40) coupled to the axle for holding the axle at a desired location. The cord is coupled between the axle and the halter. The pulley is attached to the curved section of the frame, the cord extending through the pulley between the halter and the tensioner assembly. A device for measuring the tension in the cord is also disclosed. The measuring device (48) is coupled to the cord and has an indicator to signal when the tension in the cord reaches a predetermined amount.

22 Claims, 5 Drawing Sheets

OTHER PUBLICATIONS

Granberg International, *Granberg Traction Systems: Designed for Professional and Home Treatment.*

Lossing Orthopedic, *Lossing Necktrac Assembly and Usage Guide,* 1989.

Granberg International, *E–Z Tract Set–Up Alternatives.*

Lossing Orthopedic, *The Team That Works for You,* 1992, pp. 1–13.

Saunders Therapy Products, *Educational Opportunities 1991 Catalog,* 1991, pp. 1–63.

Lossing Orthopedic, *Lossing Cervical Treatment Systems,* 1990.

Lossing Orthopedic, *Lossing Necktrac Assembly and Use Guide,* 1991.

CERVICAL TRACTION DEVICE

FIELD OF THE INVENTION

This invention relates to traction devices and, in particular, to a portable cervical traction device that can be operated by the person being subjected to traction.

BACKGROUND OF THE INVENTION

Effective traction devices for cervical traction are commonly used in hospitals, physical therapy centers, and other medical facilities. However, these devices are both complicated and expensive, typically utilizing electrically controlled winch systems mounted on specially constructed beds. The systems are controlled and monitored by a health care worker. They are not well suited for home or other out-patient use and are not easily portable. Persons requiring traction but otherwise not needing hospital attention would benefit from equipment that is easy to use without assistance, inexpensive, reliable, safe, and readily portable. Such equipment combined with a doctor's instructions and periodic oversight, would allow a person requiring traction to effectively administer traction to himself at home or elsewhere much more regularly and conveniently than in-patient treatment.

While some portable and patient-operable traction devices do exist, these available devices have not been entirely satisfactory in meeting all of the above-described criteria. U.S. Pat. Nos. 4,356,816 and 4,664,101 issued to Granberg disclose cervical traction devices that are operable by the patient. The first of these employs a chain and shaft mechanism within the bed of the system. The second of these devices employs a hydraulic pump mechanism to increase the tension on a cord attached to a head halter. These systems, however, may be difficult for some patients to properly set up without assistance. They can also be expensive and are large and cumbersome to carry around.

A major supplier of portable traction equipment is the Lossing Orthopedic Company of Minneapolis, Minn. The Lossing Necktrac® cervical traction device is meant to be portable for in-home use. The user of this equipment is not provided with the safety of an overload indicator or constantly visible tension readout. The user is required to pull on the cord with the full force of the desired tension to place his or her neck under the desired tension. In other words, no mechanical advantage is provided. Thus, the equipment may be quite difficult for many patients to use safely and effectively.

Other devices are also known in the prior art, however, like the devices discussed above, none of them are completely satisfactory in meeting the desired criteria. See, for example, U.S. Pat. Nos. 4,627,423; 5,052,378; 5,024,214; 4,538,598; 4,407,274; 4,674,485; 2,658,506; 4,987,886; 4,608,969; and 3,298,364.

SUMMARY OF THE INVENTION

The above-described drawbacks and limitations of the prior-art traction devices are largely overcome by the cervical traction apparatus of the present invention. The apparatus is operable by a user and applies traction to the neck of the user by pull applied to a halter holding the head of the user. The apparatus includes a frame and a tensioning means. The frame has a first section and a second section. The first section is generally straight and has a head end extending beneath the head of the user and a tail end extending beneath at least a portion of the back of the user. The second section generally forms a C-shape behind and above the head of the user. The second section has a lower portion, a middle portion, and an upper portion. The lower portion is coupled to the head end of the first section. The middle portion curves upwardly away from the longitudinal axis of the first section. The upper portion is generally parallel to the first section and extends over the head of the user. A tensioning means is coupled to the upper portion of the second section of the frame. The tensioning means is operable by the user of the traction apparatus and pulls on the halter. The tensioning means also preferably has a means for holding the tension at a desired level.

In the preferred embodiment of the present invention the tensioning means includes a cord and a tensioner assembly. The tensioner assembly includes an axle around which the cord is wrapped and a handle fastened to the axle. The handle has a grip radially spaced from the axle by a distance of at least one axle diameter to create a mechanical advantage during tensioning. The handle is operable by the user for rotating the axle to increase the tension in the cord and thus the force exerted on the halter. The axle is rotatably coupled to the upper portion of the second section of the frame. The cord extends from the axle to the halter through a pulley or sheave mounted on the middle portion of the second section of the frame so that a selected cord slope is achieved in the segment of the cord that spans the middle portion and the halter, thus controlling the angle at which force is applied to the halter.

The preferred embodiment of the invention also includes means for measuring the tension in the cord. The measuring means are coupled to the cord and include display means attached to the upper portion of the second section of the frame, the display means being arranged and configured to be viewed by the user. The display means are preferably digital.

In one preferred embodiment of the invention, the measuring means include a capacitance gauge attached to the span of the cord that extends between the halter and the middle portion of the second section of the frame. The measuring means further include an adjustable overload alarm that indicates when a predetermined tension has been exceeded.

In another aspect of the preferred embodiment of the invention, the holding means of the tensioning means include a pawl pivotally attached to the upper portion of the second section of the frame and ratchet projections attached to the handle. The pawl allows the handle and axle to be rotated in one direction only until deactivated by the user.

As another aspect of the preferred embodiment of the present invention, the frame also includes a shoulder brace coupled between the head end and the tail end of the first section of the frame. The shoulder brace is oriented generally transverse to the longitudinal axis of the first section of the frame. Preferably, the shoulder brace comprises two paddles connected by a narrow neck. The narrow neck is connected to the first section of the frame and the paddles extend away from the first section in a plane generally transverse to the longitudinal axis of the first section.

Preferably, the first section of the frame is detachable from the second section of the frame. The second section of the frame may be constructed of a material having a U-shaped cross section. The middle portion of the second section has a smoothly curved shape. Adjustment means are coupled to the second section of the frame and to the cord for adjusting the angle of that span of the cord that is coupled to the halter relative to the first section of the frame.

In another preferred aspect of the device of the present invention, the tail end of the first section of the frame is pivotally attached to the underside of the head end between the shoulder brace and the attachment to the second section. This allows the tail end to provide support to counter the tension in the cord when the tail end is swung into an extended position. This arrangement also provides for a more compact first section when the tail end is swung into a retracted position next to the head end.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
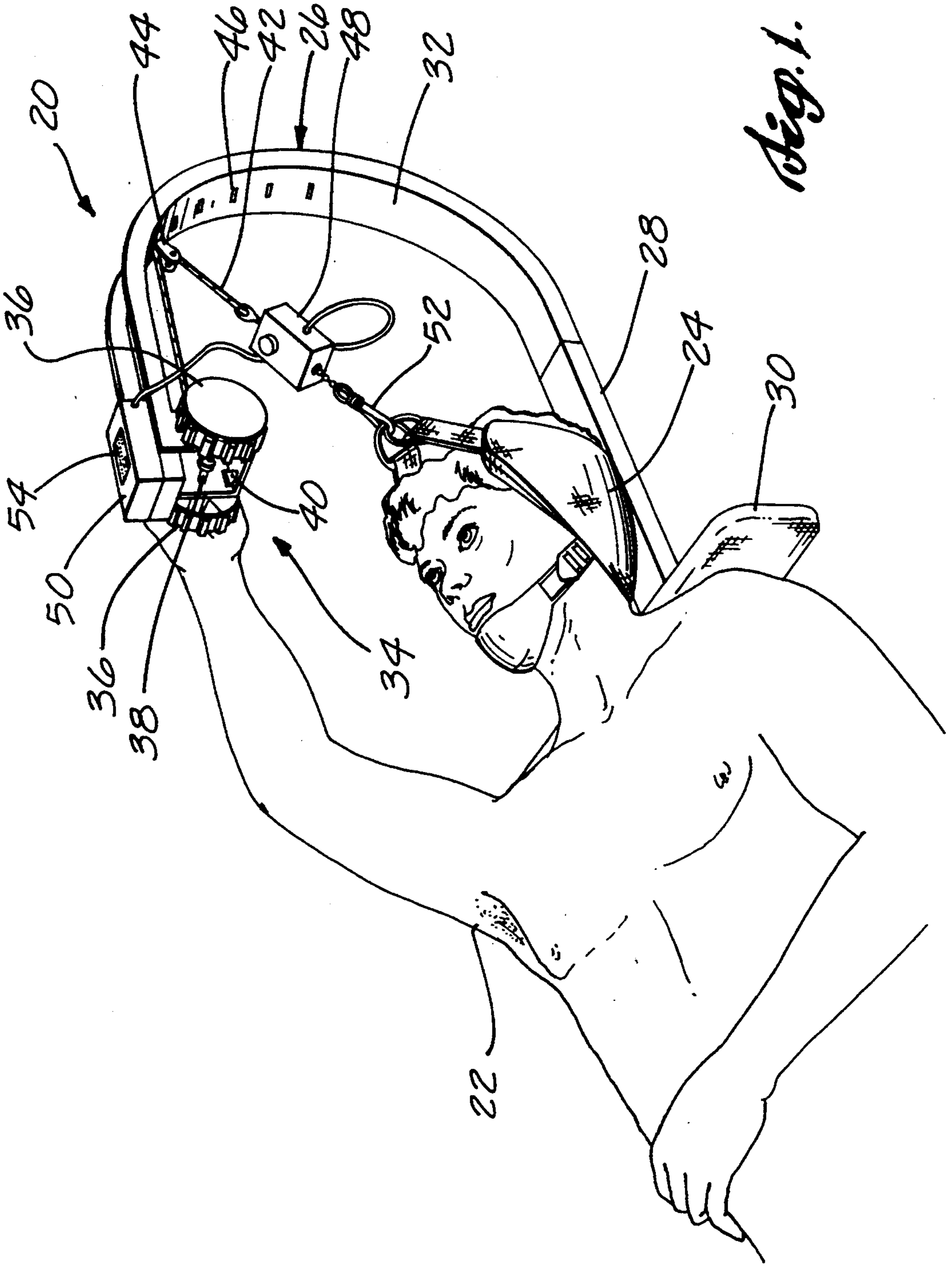
FIG. 1 is a perspective view of the cervical traction device of the present invention showing the use of the device with a patient.
Figure 2:
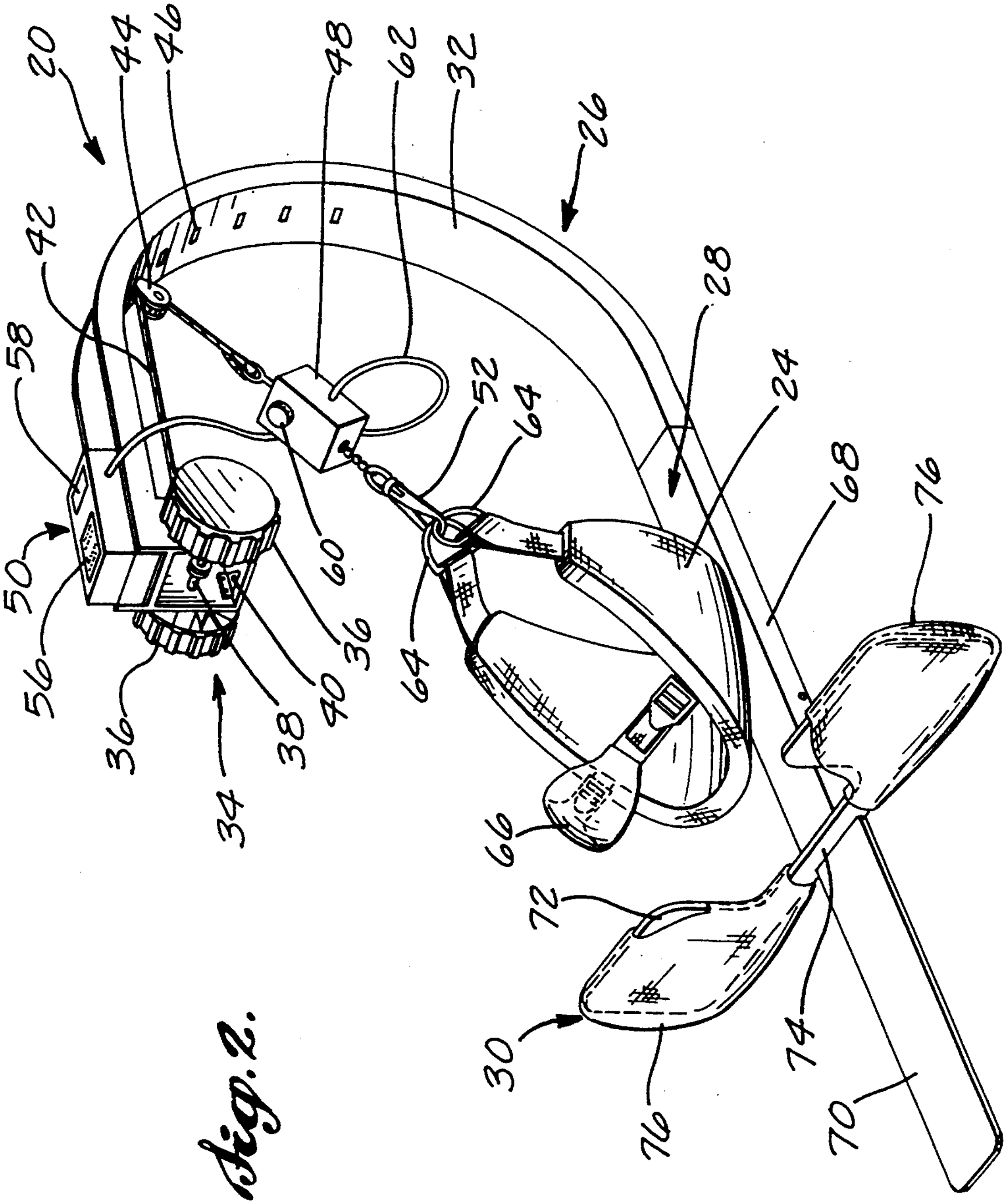
FIG. 2 is a perspective view of the device of the present invention similar to that of FIG. 1, but not including the patient.

FIGS. 1 and 2 illustrate the basic arrangement of the cervical traction device 20 of the present invention. The preferred embodiment of cervical traction device 20 is arranged and configured to be assembled on a bed or floor; a halter 24 is placed on the patient's head, and the patient lies down on his back for cervical traction with the device. This explanation assumes that the preferred embodiment of cervical traction device 20 is used, such that patient 22 is lying on his back. However, the same basic arrangement of cervical traction device 20 can be used with the patient in upright or other positions.

Cervical traction device 20 includes a frame 26 having a straight section 28, a shoulder brace 30, and a curved section 32. Preferably, frame 26 is constructed of extruded 6061 aluminum channel having a U cross-sectional shape. However, it should be understood that other materials and cross-sectional shapes could be used. Frame 26 is coated with a durable and scratch-resistant powder-coated polyurethane paint. Straight section 28 extends beneath the head and a portion of the back of the user. Straight section 28 has a longitudinal axis directly beneath patient 22 parallel to the longitudinal axis of patient 22. Shoulder brace 30 is attached to straight section 28 transverse to the longitudinal axis of straight section 28. The function of shoulder brace 30 is to restrain patient 22 from excessive movement while being in traction. This arrangement reduces the variance in the tension applied to the neck of patient 22. Curved section 32 is attached to one end of straight section 28 behind the head of patient 22. Curved section 32 forms a C-shape having its open side facing patient 22 such that, while cervical traction device 20 is in use, curved section 32 arches behind and around the head of patient 22. The upper portion of curved section 32 extends to a position above and only slightly behind the forehead of patient 22.

A tensioner assembly 34 is attached to the end of the upper portion of curved section 32 above the head of patient 22. The function of tensioner assembly 34 is to allow patient 22 to increase or decrease the tension being placed on his neck through halter 24. Tensioner assembly 34 includes handles 36, axle 38, and ratchet mechanism 40. Handles 36 are located on either side of the end of curved section 32 such that they are readily accessible by either hand of patient 22 for adjustment purposes. Preferably, handles 36 are disk-shaped and substantially larger in diameter than axle 38 to provide ease of adjustment for patient 22. Axle 38 connects handles 36 together and to curved section 32 of frame 26. Ratchet mechanism 40 ensures that handles 36 and axle 38 are rotated in only one direction for tensioning and are held at a desired position until released.

A cord 42 is secured to axle 38 such that, as axle 38 is rotated through the use of handles 36, cord 42 wraps around axle 38. Cord 42 extends to halter 24 such that, when cord 42 is pulled by wrapping around axle 38, tension is increased on halter 24 and, thus, the neck of patient 22. Cord 42 extends from axle 38 to a pulley 44, which is removably attached to the middle portion of curved section 32 of frame 26. Pulley 44 is a standard pulley having a stirrup holding a wheel with a gored rim. It will be understood that other conventional means of adjustably mounting a roller or sheave to section 32 to control the angle of cord 42 may also be used. For example, rollers adapted to receive and turn cord 42 could be mounted directly in appropriately shaped openings in section 32. Pulley 44 can be positioned in any of openings 46 that are disposed at discrete locations along the middle portion of curved section 32. Any number of openings 46 could be used along curved section 32. The purpose of having multiple openings 46 in curved section 32 is to provide for multiple angles of cord 42 between pulley 44 and halter 24. Preferably, the angle of cord 42 between pulley 44 and halter 24 can be adjusted between 15 degrees and 45 degrees.

Figure 5:
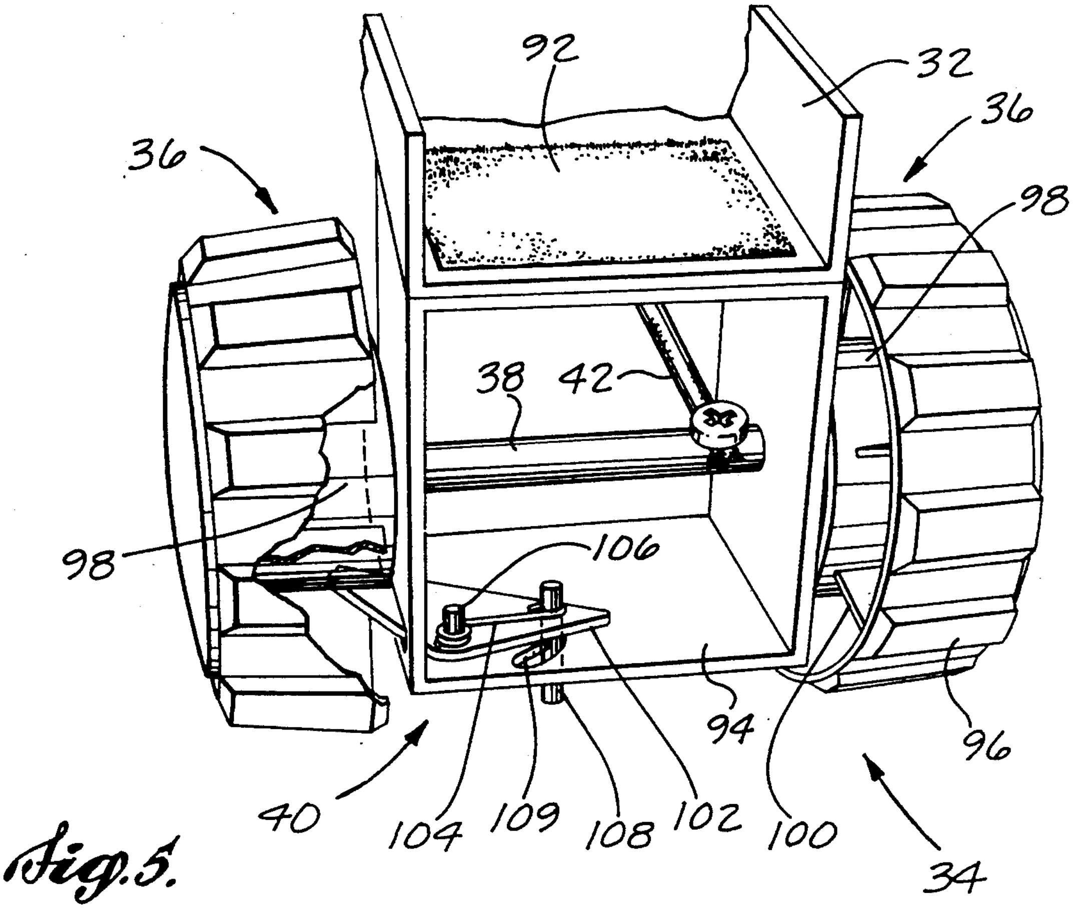
FIG. 5 is a perspective view of the tensioner assembly illustrating the ratchet mechanism.

In the preferred form of the invention, cord 42 is coupled to halter 24 through a capacitance gauge 48. Capacitance gauge 48 is attached on one end to cord 42 and on the other end to halter 24. Capacitance gauge 48 is calibrated to measure the tension in cord 42, which is a measure of the traction being placed on the neck of patient 22. The basic internal construction of capacitance gauge 48 is explained in Christman et al. U.S. Pat. No. 4,936,399. Capacitance gauge 48 in the preferred form of the present invention has been modified slightly to be used with cervical traction device 20 and to include a display 50 separate from capacitance gauge 48 to be viewed by patient 22 as traction is being applied. Display 50 is removably positioned on the end of the upper portion of curved section 32, such that it is above the head of patient 22 easily within the range of vision of patient 22. Display 50 is removably attached to the top side of curved section 32 within the channel of curved section 32 by hook-and-loop fastening tape, such as Velcro®. This removable attachment to curved section 32 allows display 50 to be entirely removed from curved section 32 or reversed such that it can be seen by an assistant instead of patient 22, as illustrated in FIG. 1. A hook-and-loop fastening tape 54 is shown on one side of display 50 in FIG. 1. FIG. 2 shows that the other side of display 50 also has fastening tape 56 attached to it. Also, additional fastening tape 92 is shown in FIG. 5, to which fastening tape 56 and 54 may be engaged for positioning of display 50. Display 50 has generally a parallelepiped shape with a display screen 58 on one face that can be positioned for viewing by patient 22, as shown in FIG. 1, or by an assistant, as shown in FIG. 2. The size of display 50 is such that it can fit between the sides of the U-shaped channel of which curved section 32 is constructed. An electrical cable 62 interconnects display 50 with capacitance gauge 48.

Capacitance gauge 48 is connected to halter 24 with a hook 52. Hook 52 is attached to halter 24 by clipping onto D-rings 64. Halter 24 also includes a chin strap 66. It should be noted, however, that most standard halters can be used with cervical traction device 20. The specific use of any particular halter with cervical traction device 20 is within the scope of this invention.

Capacitance gauge 48 has a control knob 60 with which to set a tension overload alarm within capacitance gauge 48. This provides a measure of safety, as patient 22 can set control knob 60 at a predetermined amount of tension before applying tension to his neck. In the preferred form of the invention, an audible alarm sounds when the tension exceeds the predetermined amount selected with control knob 60. This is a redundant safety system, since display screen 58 shows the amount of tension in cord 42 at all times. Alternatively, a load-limiting clutch or other overload protection may be used. Control knob 60, as illustrated, is attached to capacitance gauge 48. However, this could also be attached separately from capacitance gauge 48. For example, control knob 60 could be attached to display 50 for viewing and control by patient 22 while in traction.

In the present preferred embodiment of the invention, the overload alarm functions with a comparator that looks at the phase difference of the AC electrical impulses that activate the display segments for the tens digit in the display screen 58. If those segments that are out of phase with the backplane phase correspond to the tens digit set with control knob 60, an oscillator is excited to make a high-pitched alarm tone.

The attachment of capacitance gauge 48 in series with cord 42 before the attachment of cord 42 to halter 24 allows for constant display and monitoring of the tension being applied. This arrangement can be advantageous as changes may occur in patient positioning or other variables while traction is being applied. These variables may change the amount of tension being applied. If large changes result, patient 22 simply readjusts the tension through the use of handles 36.

Those skilled in the art will appreciate that other types of gauges can be used in place of capacitance gauge 48. For example, a resistance gauge or even a spring scale could be used.

Other details of frame 26 are also illustrated in FIG. 2. Straight section 28 includes a head portion 68 extending from shoulder brace 30 to the connection with curved section 32. Straight section 28 also includes a tail portion 70 that extends beneath the back of patient 22 between the shoulders of patient 22. Tail portion 70 functions to provide additional support to counter the force placed on frame 26 at pulley 44 as tension in cord 42 is applied.

Shoulder brace 30 includes vertically oriented paddles 72 that rise on either side of the neck of patient 22 to provide a restraining force on the shoulders of patient 22. Paddles 72 are generally rectangular in shape, although contoured such that no sharp edges bite into the body of patient 22. A narrow brace strut 74 interconnects paddles 72 and also serves to attach shoulder brace 30 to head portion 68 of straight section 28. Pads 76 are also removably secured to paddles 72. Pads 76 are constructed of closed-cell foam covered with a cloth material. Pads 76 function to increase the comfort level of patient 22.

Figure 3:
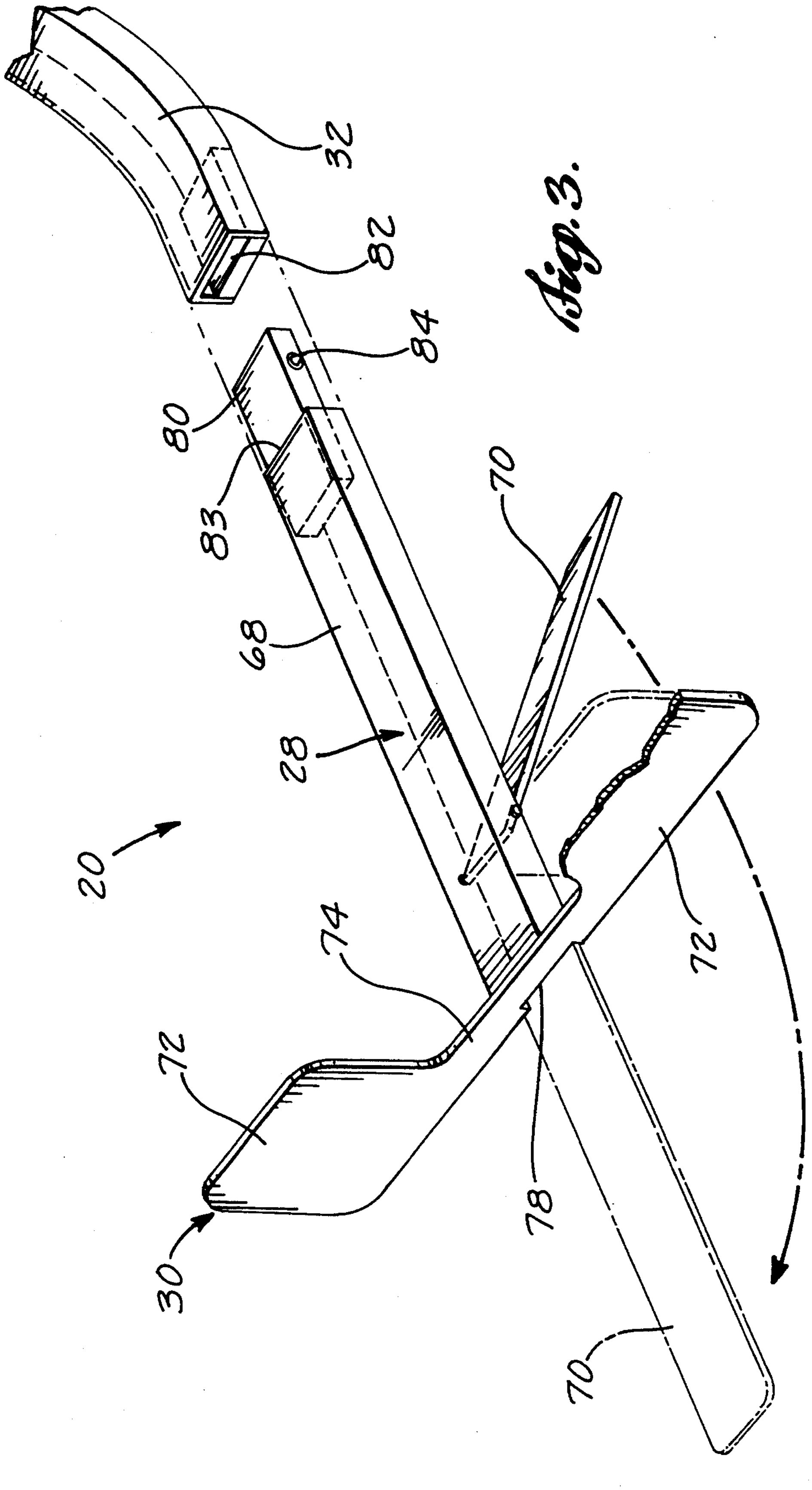
FIG. 3 is a perspective view of the straight section of the frame of the traction device of the present invention, illustrating the attachment to the curved section and the pivotal movement of the tail portion.

Referring now to FIG. 3, additional details of frame 26 will be discussed. Tail portion 70 is rectangular in shape and is formed from a flat piece of aluminum with sufficient rigidity to resist the forces placed upon it. Tail portion 70 is pivotally attached to head portion 68 behind the attachment of shoulder brace 30 to head portion 68. The pivotal attachment of tail portion 70 allows tail portion 70 to be folded up against head portion 68 when cervical traction device 20 is disassembled. This feature increases the compactness of disassembled cervical traction device 20. To put tail portion 70 to use, it is simply swung downwardly and into a recess 78 on the underside of brace strut 74. The combination of the pivotal attachment of tail portion 70 at its end with its engagement within recess 78 does not allow tail portion 70 to be rotated upwardly out of approximately linear alignment with head portion 68. Thus, tail portion 70 can resist the forces placed upon it and stabilize cervical traction device 20, while not adding to its disassembled size.

The end of straight section 28 opposite shoulder brace 30 includes a plug 80, which is arranged and configured to fit within a socket 82 on the lower end of curved section 32. Plug 80 and socket 82 provide an attachment means between straight section 28 and curved section 32 that does not allow rotational movement of curved section 32 relative to straight section 28 when the two are coupled together. Plug 80 is constructed of a block of material within the end of straight section 28, but having a smaller perimeter than that of the remainder of straight section 28 such that a shoulder 83 is formed. Shoulder 83 functions to limit the depth of insertion of plug 80 into socket 82. A detent 84 is also provided on the sides of plug 80 to prevent straight section 28 from inadvertently falling out of curved section 32. Socket 82 is formed by simply fixing a plate along a portion of the end of curved section 32 between the sides of the channel such that a rectangular opening is formed into which plug 80 may be placed.

Figure 4:
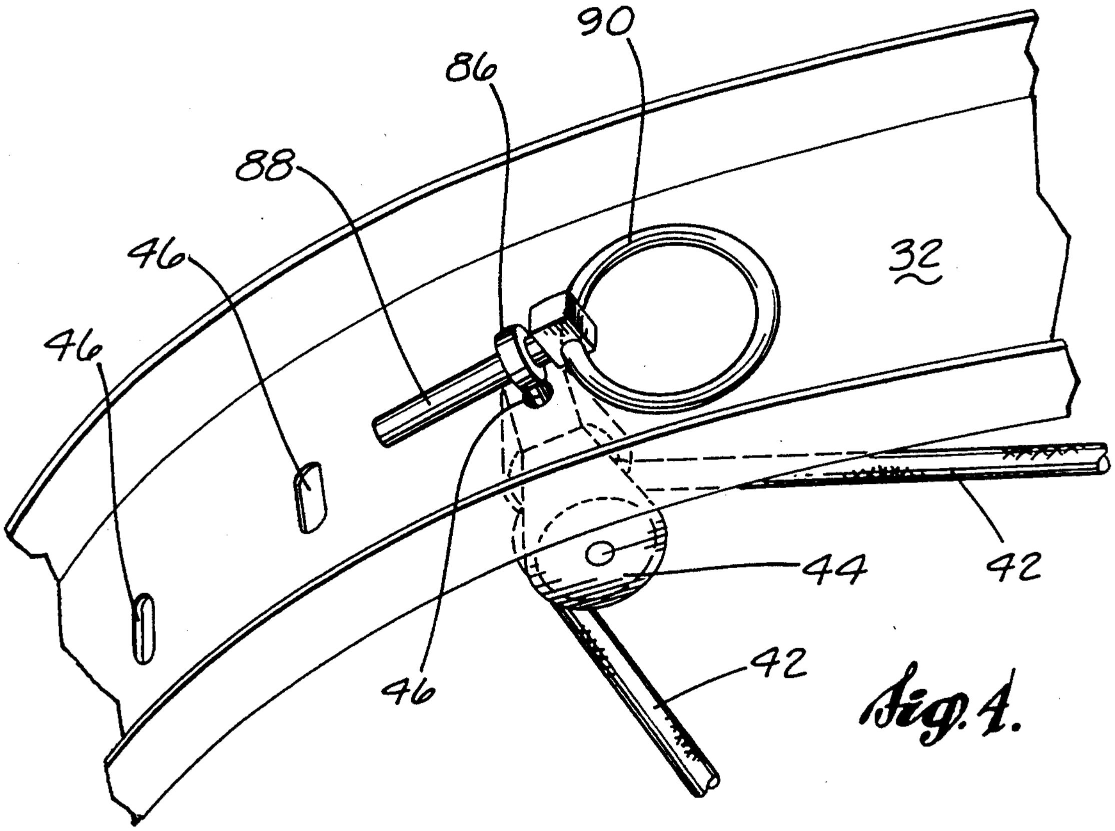
FIG. 4 is a perspective view of a portion of the curved section of the frame and the adjustable pulley system of the present invention.

Referring now to FIG. 4, the removable attachment of pulley 44 to the middle portion of curved section 32 will be discussed. Pulley 44 includes a structure forming an eye 86 projecting from its back side. Eye 86 may be inserted through any of openings 46 in curved section 32. Openings 46 are generally oval in shape and match the outer shape of eye 86. A pin 88 is provided that engages within eye 86 after eye 86 is inserted through one of openings 46. Pin 88 includes a ring 90 on its upper end to stop pin 88 from dropping all the way through and out of eye 86 and to provide a convenient place for patient 22 to grasp pin 88. With this arrangement, pulley 44 may be adjusted along the middle portion of curved section 32, preferably to be able to adjust the slope of that segment of cord 42 that extends between pulley 44 and halter 24 to a desired slope between 15 degrees and 45 degrees. Alternate adjustment systems are envisioned and within the scope of the present invention. For example, the adjustment could be accomplished by simply having a slot running parallel to curved section 32 along the middle portion of curved section 32 with pulley 44 having a clamping mechanism that engages within the slot to clamp pulley 44 into any discrete location along the middle portion of curved section 32. Other arrangements providing for adjustment of the slope of cord 42 will be obvious to those skilled in the art.

Referring now to FIG. 5, tensioner assembly 34 will be described in more detail. Tensioner assembly 34 includes handles 36, axle 38, and ratchet mechanism 40. These elements are all coupled to tensioner support member 94. Tensioner support member 94 is constructed of a simple box having top, bottom, and lateral sides and being open at both ends. Tensioner support member 94 has bores in its two lateral sides through which axle 38 is rotatably engaged. The top side of tensioner support member 94 is attached to the bottom surface of the end of curved section 32. Handles 36 include grips 96 on their outer periphery. Grips 96 are in the form of transversely oriented raised portions around the perimeter of handles 36. Hubs 98 in the central portion of handles 36 are attached to axle 38. Radially and transversely extending vanes 100 connect hubs 98 to grips 96. Vanes 100 are spaced evenly around hubs 98. Preferably, 10 vanes 100 are used, however, any number of vanes may be used. Vanes 100 not only function to provide support for grips 96, but also to be pan of ratchet mechanism 40. Ratchet mechanism 40 also includes a pawl 102 attached to the bottom side of tensioner support member 94. Pawl 102 is triangular in shape with one comer extending through a lateral side of tensioner support member 94 and engaging with vanes 100 for the ratcheting action. A spring 104 is attached to a pivot post 106 at a second comer of pawl 102. Spring 104 has one end biased against the side of tensioner support member 94 and the other end secured to an attachment post 108. Attachment post 108 extends through a slot 109 in the bottom side of tensioner support member 94, such that post 108 is movable by patient 22. Spring 104 biases the outside corner of pawl 102, which extends through the lateral side of tensioner support member 94 in an outward direction. Thus, as handles 36 are rotated in a cord-tightening direction, vanes 100 push pawl 102 out of the way and are allowed to pass, while rotation in the opposite direction places pawl 102 in interference with one of vanes 100 such that rotation is not allowed. This arrangement allows patient 22 to adjust the tension in cord 42 to a desired amount and then leave the tension set at that amount for any period of time. When patient 22 wishes to relieve the tension in cord 42, he simply needs to rotate handles 36 a small amount and pull back on the portion of attachment post 108 that extends below tensioner support member 94, such that pawl 102 does not engage any of vanes 100. He can then slowly relieve the tension in cord 42 by rotation of handles 36. The large diameter of handles 36 provides a high mechanical advantage when applying tension to cord 42. This mechanical advantage allows any adjustments, large or small, to be easily made by patient 22.

Figure 6:
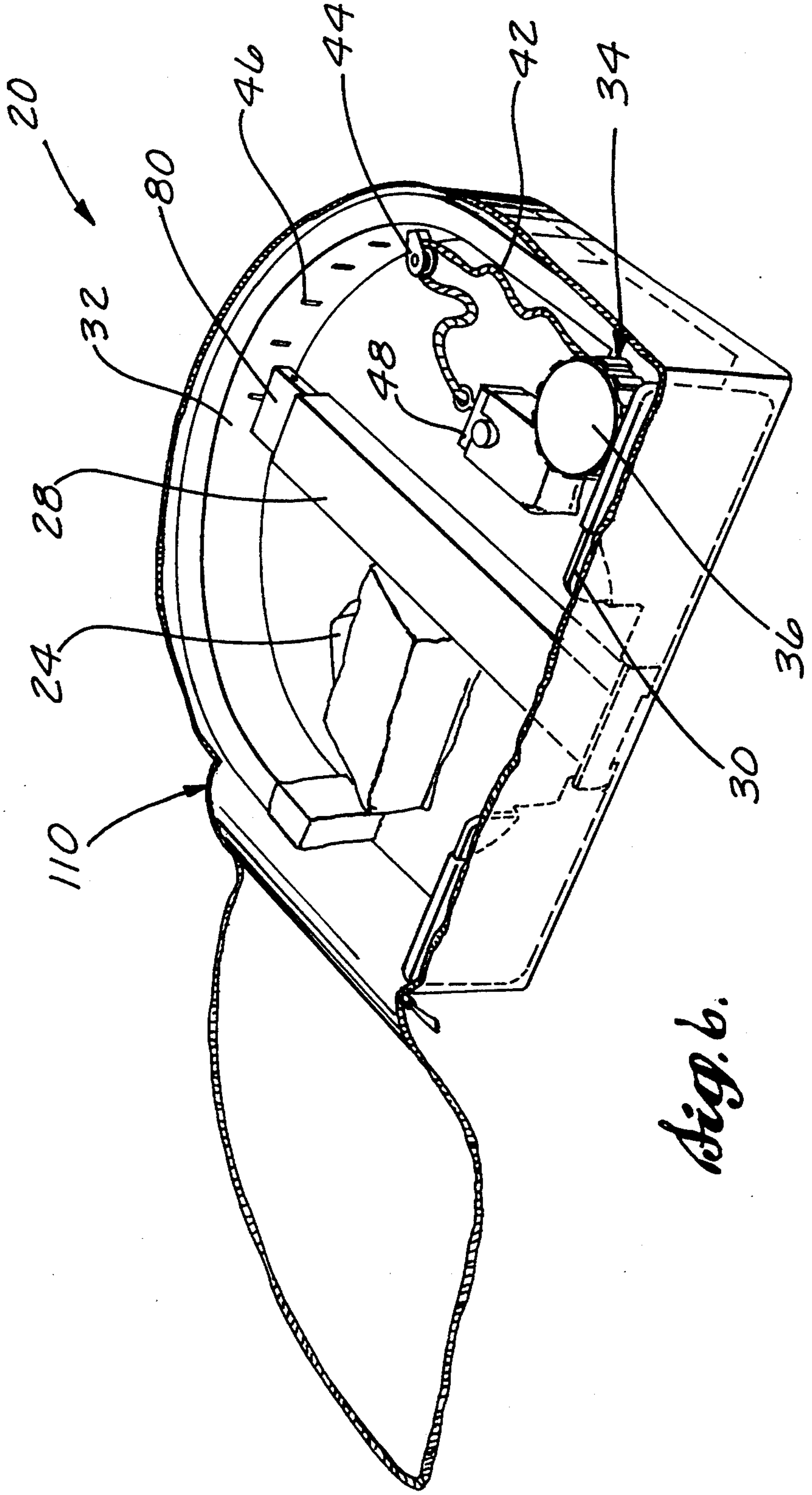
FIG. 6 is a perspective view of the traction device of the present invention in a disassembled, compact configuration suitable for storage or transport.
Figure 1:
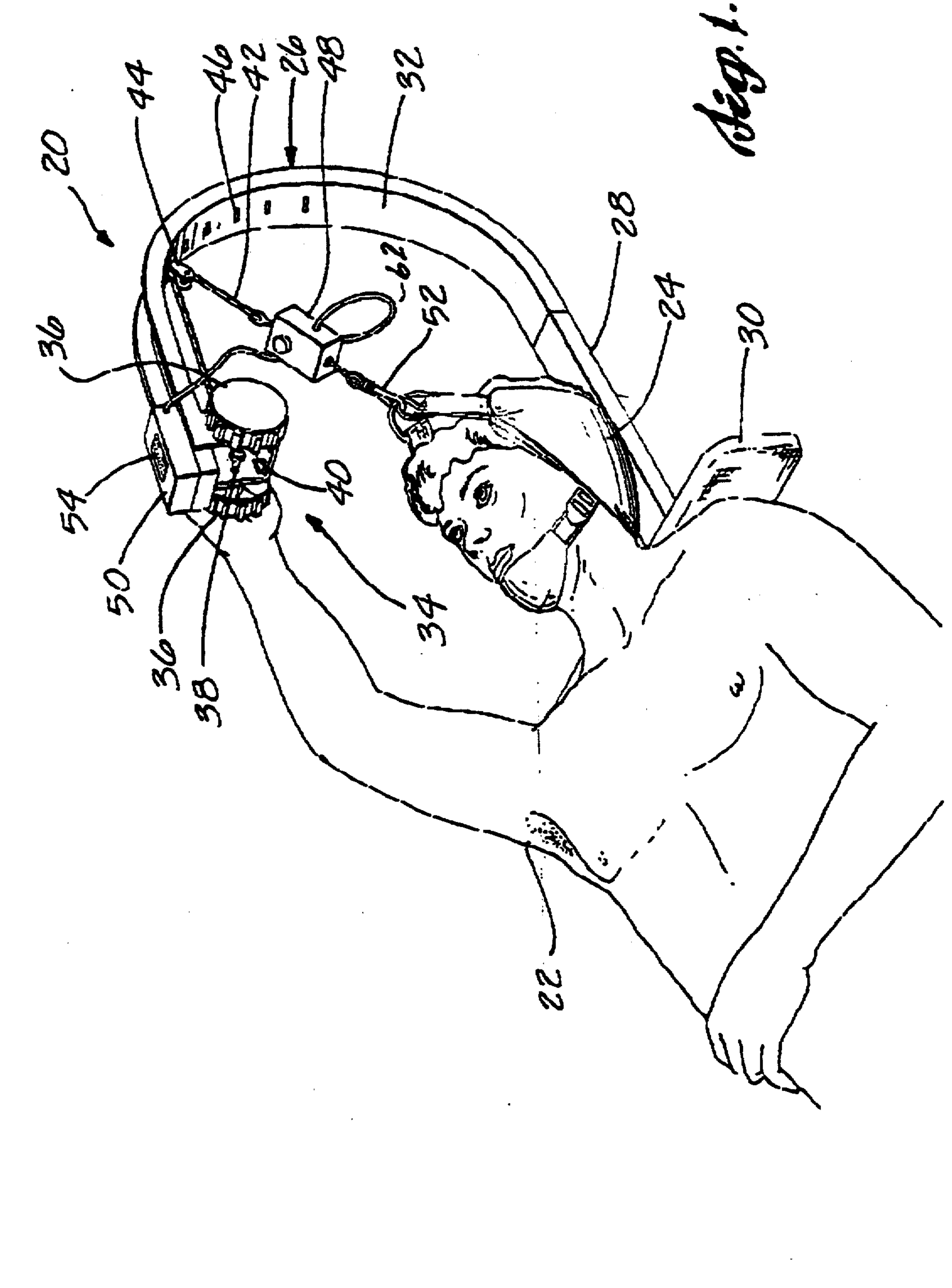

The advantages of disassembly and compactness of cervical traction device 20 are seen in FIG. 6. Once patient 22 removes halter 24 from hook 52, he can disassemble and store or transport cervical traction device 20 with ease. Patient 22 simply disconnects plug 80 from socket 82 to remove curved section 32 from straight section 28. Tail portion 70 is swung up next to head portion 68 and the entire assembly may be fit in a compact shape within a case 110, such as that shown in FIG. 6. Case 110 simply surrounds curved section 32 with straight section 28 and shoulder brace 30 nested within curved section 32. Preferably, pockets are provided within case 110 for holding halter 24, capacitance gauge 48, and display 50. Thus, not only is cervical traction device 20 easy to use, but it is also easy to transport and store.

The compactness of cervical traction device 20 makes it advantageous for use in medical facilities as well as for in-home use. For example, a physical therapy center with limited space may appreciate the ability to fold cervical traction device 20 into a compact size for easy storage when not in use. With the simple setup procedure, cervical traction device 20 can be set up on a patient table or other location quickly and easily when needed.

While several advantageous features of cervical traction device 20 have been discussed above, other advantages are also evident. For example, since the construction of cervical traction device 20 is so simple, the device is lightweight and easy to assemble. The user simply needs to swing out tail portion 70 and attach straight section 28 onto the end of curved section 32. Patient 22 may wish to set control knob 60 to activate the overload alarm before clipping halter 24 onto hook 52. Patient 22 then controls the tension by using handles 36 together with ratchet mechanism 40. At all times patient 22 can be aware of the tension being applied by reading display screen 58. Pawl 102 is easy to deactivate, since attachment post 108 extends through the bottom surface of tensioner support member 94 to be in plain sight of patient 22, and easy to use by simply moving attachment post 108.

The forces acting on cervical traction device 20 are all generally within a vertical plane extending through the longitudinal axis of patient 22 and straight section 32. The smooth construction of curved section 32 also smoothes out the forces applied to all of frame 26 such that no high-stress concentrations are formed. No welded supports need be used either. Cervical traction device 20 is preferably constructed to safely and reliably operate under at least 50 pounds of tensile force in cord 42. Lateral stability is assured by the transverse arrangement of shoulder brace 30. Any lateral forces would necessarily be transmitted from the head of patient 22, which is positioned between paddles 72 of shoulder brace 30, such that stability is assured.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A cervical traction apparatus operable by a user for applying traction force to the neck of the user, the apparatus comprising:

(a) a halter for holding the head of the user;

(b) a frame having a first section and a second section, the first section being generally straight and having a head portion adapted to extend beneath the head of the user and a tail portion adapted to extend beneath at least a portion of the back of the user, the second section having a lower portion coupled to the head portion of the first section, a middle portion extending away from the longitudinal axis of the first section, and an upper portion adapted to extend to a position generally above the head of the user; and (c) tensioning means operable by the user of the traction apparatus for applying traction force on the halter, said tensioning means being coupled to said frame and said halter and having means for adjusting and holding the traction force at a desired level, wherein said tensioning means includes a cord, an attachment means for coupling the cord to the middle portion, and a tensioner assembly, said tensioner assembly including an axle around which said cord is wrapped and a handle coupled to the axle, the handle having a grip radially spaced from the axle by a distance of at least one axle diameter, the handle being operable by the user for rotating the axle to increase the tension in the cord, the axle being rotatably coupled to the upper portion of the second section of the frame, the cord extending from the axle to the halter and being coupled to the middle portion of the second section of the frame so that a desired cord slope is achieved in the segment of the cord that spans the middle portion and the halter.

2. The apparatus of claim 1, further including means for measuring the tension in the cord, said measuring means being coupled to the cord, said measuring means including display means attached to the upper portion of the second section of the frame, the display means being arranged and configured to be viewed by the user during traction.

3. The apparatus of claim 2, wherein said display means are digital.

4. The apparatus of claim 2, wherein said measuring means include a capacitance gauge attached to the span of the cord that extends between the halter and the middle portion of the second section of the frame.

5. The apparatus of claim 2, wherein said measuring means further include an adjustable overload alarm that indicates when a predetermined tension has been exceeded.

6. The apparatus of claim 1, wherein the holding means comprise a pawl pivotally attached to the upper portion of the second section of the frame and ratchet projections attached to the handle, the pawl allowing the handle and axle to be rotated in one direction only until deactivated by the user.

7. The apparatus of claim 1, wherein the frame further comprises a shoulder brace coupled between the head portion and the tail portion of the first section of the frame and being oriented generally transverse to the longitudinal axis of the first section.

8. The apparatus of claim 7, wherein said first section of said frame is detachable from said second section of said frame.

9. The apparatus of claim 8, wherein the second section of said frame is constructed of a material having a U-shaped cross section, and wherein the middle portion of the second section has a "C" shape.

10. The apparatus of claim 9, further including adjustment means coupled to the second section of the frame and to the cord for adjusting the angle of that span of the cord running from the adjustment means to the halter.

11. The apparatus of claim 10, wherein the tail portion of the first section of the frame is pivotally attached to the underside of the head portion between the shoulder brace and the attachment to the second section, such that the tail portion provides stabilizing structural support when swung into an extended position and provides for a more compact first section when swung into a retracted position for storage.

12. The apparatus of claim 7, wherein the tail portion of the first section of the frame is pivotally attached to the underside of the head portion, such that the tail portion provides structural support when swung into an extended position during application of traction force and provides for a more compact first section when swung into a retracted position next to the head portion.

13. The apparatus of claim 7, wherein the shoulder brace comprises two paddles connected by a narrow neck, the narrow neck being connected to the first section of the frame, the paddles extending away from the first section in a plane generally transverse to the longitudinal axis of the first section.

14. The apparatus of claim 11, further comprising adjustment means coupled to the second section of the frame and the cord for adjusting the angle of the span of the cord that is coupled to the halter relative to the first section of the frame.

15. The apparatus of claim 14, wherein said adjustment means comprise a plurality of openings longitudinally spaced along the middle portion of the second section of said frame, a pulley coupled to the cord and having means for removably mounting the pulley in one of the plurality of openings.

16. An apparatus for applying cervical traction to a user, the apparatus comprising:

(a) a head halter;

(b) a frame having a generally straight section, a curved section, and a shoulder brace, the straight section having a head portion adapted to extend beneath the head of the user and a tail portion adapted to extend beneath at least a portion of the back of the user, the shoulder brace being coupled to the straight section and being oriented generally transverse to the longitudinal axis of the straight section, the shoulder brace comprising substantially rigid transversely extending members to hold the shoulders of the user, the curved section generally forming a C shape opening toward the head of the user;

(c) a tensioner assembly coupled to the curved section and having a portion configured to be above the head of the user, the tensioner assembly including a rotatable axle, a handle attached to the axle, the handle being generally in front of the face of the user, and means for holding the rotated axle at a desired location;

(d) a cord coupled between the axle and the halter, said cord adapted to be wound on the axle to increase the tension in the cord; and (e) pulley means attached to the curved section of the frame for changing the direction of the cord, the cord extending through the pulley means between the halter and the tensioner assembly.

17. The apparatus of claim 16, further including means for measuring the tension in the cord, said measuring means being coupled to the cord, said measuring means having indicator means to indicate when the tension in the cord reaches a predetermined amount.

18. The apparatus of claim 16, further including adjustment means for adjusting the slope of the segment of the cord between the halter and the pulley means, the adjustment means including at least one slot in the curved section of the frame.

19. The apparatus of claim 16, wherein the straight section of the frame is detachable from the curved section of the frame, and wherein the tail portion of the straight section of the frame is pivotally attached to the back side of the head portion such that the tail portion is extendable and retractable by swinging the tail portion relative to the head portion.

20. An apparatus for applying cervical traction to a user, the apparatus comprising:

(a) a head halter;

(b) a frame having a generally straight section, a curved section, and a shoulder brace, the straight section having a head portion adapted to extend beneath the head of the user and a tail portion adapted to extend beneath at least a portion of the back of the user, the shoulder brace being coupled to the straight section and being oriented generally transverse to the longitudinal axis of the straight section, the curved section generally forming a C shape opening toward the head of the user;

(c) a tensioner assembly coupled to the curved section and having a portion configured to be above the head of the user, the tensioner assembly including a rotatable axle, a handle attached to the axle, and means for holding the rotated axle at a desired location;

(d) a cord coupled between the axle and the halter, said cord adapted to be wound on the axle to increase the tension in the cord;

(e) pulley means attached to the curved section of the frame for changing the direction of the cord, the cord extending through the pulley means between the halter and the tensioner assembly; and (f) means for measuring the tension in the cord, said measuring means being coupled to the cord, said measuring means having indicator means to indicate when the tension in the cord reaches a predetermined amount, wherein the indicator means includes display means attached to the end of the curved section of the frame opposite the attachment to the straight section such that the display means is in the line of sight of the user.

21. An apparatus for applying cervical traction to a patient, the apparatus comprising:

(a) a frame having a generally straight section and a curved section, the straight section have a head portion adapted to extend beneath the head of the user and a tail portion adapted to extend beneath at least a portion of the back of the user and the curved section generally forming a C shape opening toward the head of the user;

(b) a tensioning means coupled to said frame for applying traction to the neck of the patient;

(c) a control means coupled to said frame and to said tensioning means for providing patient control of the traction applied, said control means providing a mechanical advantage to the patient in adjusting the traction applied by the tensioning means; and (d) an indicator means coupled to said tensioning means for continuously indicating to the patient the mount of tension being applied by the tensioning means, the indicator means including display means attached to the end of the curved section of the frame opposite the attachment to the straight section, such that the display means are in the line of sight of the user.

22. The apparatus of claim 21, further comprising an alarm means for indicating when the tension has exceeded a desired amount, said alarm means being coupled to said tensioning means.

* * * * *

UNITED STATES PATENT AND TRADEMARK OFFICE

CERTIFICATE OF CORRECTION

PATENT NO. : 5,451,202

DATED : September 19, 1995

INVENTOR(S) : F.A. Miller, et al

It is certified that error appears in the above-indentified patent and that said Letters Patent is hereby corrected as shown below:

The title page, showing the illustrative figure, should be deleted and substitute therefor the attached title page.

Delete Drawing Sheet 1, and substitute therefor the attached Drawing Sheet 1, consisting of Figure 1, showing the insertion of reference numeral "62".

| Column | Line | |
|---|---|---|
| 7 | 36 | "pan" should read --part-- |
| 7 | 39 | "comer" should read --corner-- |
| 7 | 42 | "comer" should read --corner-- |
| 10 (Claim 14, | 27 line 1) | "11," should read --1,-- |
| 12 (Claim 21, | 15 line 4) | "have" should read --having-- |

United States Patent [19]
Miller et al.

[11] Patent Number: 5,451,202
[45] Date of Patent: Sep. 19, 1995

[54] CERVICAL TRACTION DEVICE

[75] Inventors: Forrest A. Miller; Robert T. Cardozo, both of Seattle, Wash.

[73] Assignee: Pacific Research Laboratories, Inc., Vashon, Wash.

[21] Appl. No.: 125,471

[22] Filed: Sep. 22, 1993

[51] Int. Cl.$^6$ .................... A61F 5/00
[52] U.S. Cl. .................... 602/36; 602/35; 606/241
[58] Field of Search .................... 602/18, 32, 33, 35, 602/36; 601/39; 606/241

[56] References Cited

U.S. PATENT DOCUMENTS

| | | | |
|---|---|---|---|
| 2,633,125 | 3/1953 | Yellin . | |
| 2,658,506 | 11/1953 | Haskell . | |
| 2,940,441 | 6/1960 | Demarest et al. | 602/32 |
| 2,954,026 | 9/1960 | Spinks | 602/32 |
| 3,063,445 | 11/1962 | Ries | 602/32 |
| 3,298,364 | 1/1967 | Radford . | |
| 3,359,976 | 12/1967 | Laval, Jr. | 602/36 |
| 3,662,750 | 5/1972 | Jorgensen | 602/35 |
| 3,856,003 | 12/1974 | Pfluger | 602/33 |
| 4,257,410 | 3/1981 | Flewelling . | |
| 4,282,868 | 8/1981 | Riggs . | |
| 4,356,816 | 11/1982 | Granberg . | |
| 4,407,274 | 10/1983 | Goodley . | |
| 4,466,427 | 8/1984 | Granberg . | |
| 4,531,514 | 7/1985 | McDonald et al. . | |
| 4,534,341 | 8/1985 | Bart et al. . | |
| 4,538,598 | 9/1985 | Gill et al. . | |
| 4,602,619 | 7/1986 | Wolf et al. . | |
| 4,603,689 | 8/1986 | Horner . | |
| 4,608,969 | 9/1986 | Hamlin . | |
| 4,627,423 | 12/1986 | Kampner . | |
| 4,664,101 | 5/1987 | Granberg . | |
| 4,674,485 | 6/1987 | Swanson . | |
| 4,936,399 | 6/1990 | Christman et al. . | |
| 4,971,043 | 11/1990 | Jones | 602/36 |
| 4,987,886 | 1/1991 | McDonald et al. . | |
| 5,024,214 | 6/1991 | Hayes . | |
| 5,052,378 | 10/1991 | Chitwood . | |

FOREIGN PATENT DOCUMENTS

| | | | |
|---|---|---|---|
| 2640500 | 6/1990 | France | 602/36 |
| 2004219 | 12/1993 | Russian Federation | 602/36 |

OTHER PUBLICATIONS

"Braces Today", a Newsletter of the Pope Foundation, Inc., Feb. 1958.

(List continued on next page.)

*Primary Examiner*—Richard J. Apley
*Assistant Examiner*—Jeanne M. Clark
*Attorney, Agent, or Firm*—Christensen, O'Connor, Johnson & Kindness

[57] ABSTRACT

An apparatus for applying cervical traction to a user (22) with a head halter (24) is disclosed. The apparatus includes a frame (24), a tensioner assembly (34), a cord (42), and a pulley (44). The frame has a generally straight section (28), a curved section (32), and a shoulder brace (30). The straight section has a head portion (68) extending behind the head of the user and a tail portion (70) extending behind at least a portion of the back of the user. The shoulder brace is coupled to the straight section at the end of the head portion opposite the connection to the curved section and is oriented generally transverse to the longitudinal axis of the straight section. The curved section generally forms a C-shape. The C-shape of the curved section opens toward the head of the user. The tensioner assembly is coupled to the end of the curved section opposite the attachment to the straight section. The tensioner assembly is also coupled to the halter through the cord. The tensioner assembly includes a rotatable axle (38), a handle (36) attached to the axle, and a ratchet mechanism (40) coupled to the axle for holding the axle at a desired location. The cord is coupled between the axle and the halter. The pulley is attached to the curved section of the frame, the cord extending through the pulley between the halter and the tensioner assembly. A device for measuring the tension in the cord is also disclosed. The measuring device (48) is coupled to the cord and has an indicator to signal when the tension in the cord reaches a predetermined amount.

22 Claims, 5 Drawing Sheets

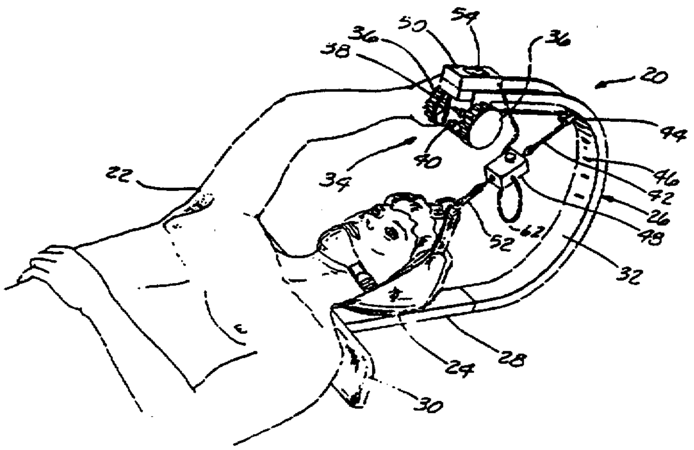

UNITED STATES PATENT AND TRADEMARK OFFICE

CERTIFICATE OF CORRECTION

PATENT NO. : 5,451,202

DATED : September 19, 1995

INVENTOR(S) : F.A. Miller, et al

It is certified that error appears in the above-indentified patent and that said Letters Patent is hereby corrected as shown below:

| Column | Line | |
|---|---|---|
| 12 (Claim 21, line 19) | 30 | "mount" should read --amount-- |

Signed and Sealed this

Twenty-sixth Day of March, 1996

Attest:

BRUCE LEHMAN

*Attesting Officer*

*Commissioner of Patents and Trademarks*